(12) United States Patent
Marash et al.

(10) Patent No.: US 9,981,145 B2
(45) Date of Patent: May 29, 2018

(54) METHOD AND APPARATUS FOR EVALUATING A CHANGE IN RADIATION DISTRIBUTION WITHIN A TARGET TISSUE

(71) Applicant: P-Cure, Ltd., Lod (IL)

(72) Inventors: Michael Marash, Rishon Le'tzion (IL); Boris Roikhel, Herzliya (IL)

(73) Assignee: P-CURE LTD., Lod (IL)

( * ) Notice: Subject to any disclaimer, the term of this patent is extended or adjusted under 35 U.S.C. 154(b) by 391 days.

(21) Appl. No.: 14/426,749

(22) PCT Filed: Sep. 24, 2013

(86) PCT No.: PCT/IL2013/050798
§ 371 (c)(1),
(2) Date: Mar. 8, 2015

(87) PCT Pub. No.: WO2014/049595
PCT Pub. Date: Apr. 3, 2014

(65) Prior Publication Data
US 2015/0238779 A1    Aug. 27, 2015

Related U.S. Application Data

(60) Provisional application No. 61/705,165, filed on Sep. 25, 2012.

(51) Int. Cl.
*A61N 5/10* (2006.01)
(52) U.S. Cl.
CPC ......... *A61N 5/1071* (2013.01); *A61N 5/1037* (2013.01); *A61N 5/1039* (2013.01);
(Continued)

(58) Field of Classification Search
CPC .. A61N 5/1049; A61N 5/1064; A61N 5/1069; A61N 5/1037; A61N 2005/1085;
(Continued)

(56) References Cited

U.S. PATENT DOCUMENTS 6,736,831 B1 * 5/2004 Hartmann ............ A61N 5/1043
607/1
2005/0096515 A1 * 5/2005 Geng ................... A61N 5/1049
600/315

(Continued)

OTHER PUBLICATIONS

International Search Report for PCT/IL2013/050798 dated Jan. 30, 2014 by Israel Patent Office.
(Continued)

*Primary Examiner* — Christine H Matthews
*Assistant Examiner* — Joshua D Lannu
(74) *Attorney, Agent, or Firm* — Chanoch Kahn; Simon Kahn

(57) ABSTRACT

An apparatus for evaluating a change in radiation distribution within a target tissue of a patient, the apparatus constituted of: a memory having stored thereon parameters of radiation to be output by an irradiation source, the radiation parameters determined responsive to a reference image of the patient target tissue; a processor in communication with the memory; and an output module in communication with the processor, wherein the processor is arranged to: receive a present image of the patient target tissue; determine the expected distribution of radiation within the patient target tissue for an irradiation incidence according to the stored radiation parameters; determine the difference between the determined distribution and a predetermined distribution parameter; and control the output module to output a signal responsive to the determined difference.

18 Claims, 2 Drawing Sheets

(52) U.S. Cl.
    CPC ......... *A61N 5/1049* (2013.01); *A61N 5/1064* (2013.01); *A61N 5/1065* (2013.01); *A61N 5/1069* (2013.01); *A61N 2005/1074* (2013.01); *A61N 2005/1085* (2013.01); *A61N 2005/1087* (2013.01)

(58) Field of Classification Search
    CPC .......... A61N 2005/1087; A61N 5/1039; A61N 5/1071; A61N 2005/1074; A61N 5/1065
    See application file for complete search history.

(56) References Cited

U.S. PATENT DOCUMENTS

| | | | | |
|---|---|---|---|---|
| 2007/0041499 A1* | 2/2007 | Lu | ......................... | A61N 5/103 378/65 |
| 2010/0086183 A1* | 4/2010 | Vik | ..................... | A61N 5/1031 382/128 |
| 2012/0123183 A1 | 5/2012 | Lavi et al. | | |
| 2012/0123184 A1* | 5/2012 | Otto | ..................... | A61N 5/1067 600/1 |

OTHER PUBLICATIONS

Written Opinion of the International Searching Authority for PCT/IL2013/050798 dated Jan. 30, 2014 by Israel Patent Office.

M. Petterson et al; "Proton Radiography Studies for Proton CT"; Published in Nuclear Science Symposium Conference Record, pp. 2276-2280, Oct. 29, 2006-Nov. 1, 2006, IEEE, New York.

Linda Hong et al; "A Pencil Beam Algorithm for Proton Dose Calculations"; Published in Phys. Med. Biol., Issue 8 (41), pp. 1305-1330, Aug. 1996, IOP Publishing, UK.

Rehnard W Schulte; "Proton Computed Tomography for Clinical Applications", Jan. 2002, published by Santa Cruz Institute for Particle Physics, Santa Cruz, California.

* cited by examiner

TO STAGE 1030

METHOD AND APPARATUS FOR EVALUATING A CHANGE IN RADIATION DISTRIBUTION WITHIN A TARGET TISSUE

TECHNICAL FIELD

The invention relates generally to the field of teletherapy and in particular to a method and apparatus for evaluating a change in radiation distribution within a target tissue.

BACKGROUND OF THE INVENTION

Teletherapy is defined as a treatment methodology in which an irradiation source is at a distance from the body to be treated. X-rays and electron beams have long been used in teletherapy to treat various cancers. Unfortunately, X-rays exhibit a linear energy transfer approaching an exponential attenuation function, and are therefore of minimal safe use for deeply embedded growths. The use of heavy particles, particularly hadrons and more particularly protons, in teletherapy has found increasing acceptance, due to the ability of heavy particles to penetrate to a specific depth without appreciably harming intervening tissue. In particular, the linear energy transfer of hadrons exhibits an inversed depth profile with a marked Bragg peak defined as the point at which the hadrons deposit most of their energy, and occurs at the end of the hadrons path. As a result of this effect, increased energy can be directed at an embedded growth as compared to X-rays and electron beams, which particularly harm intervening tissues. While the term hadrons include a wide range of particles, practically, protons and various ions are most widely used in therapy. For clarity, this document will describe treatment as being accomplished with protons, however this is not meant to be limiting in any way.

The protons or ions can be focused to a target volume of variable penetration depth. In this way the dose profile can be matched closely to the target volume with a high precision. In order to ensure complete irradiation of the target growth, a plurality of beams arriving at the embedded growth from several different directions is preferred. The point at which the plurality of beams intersects, whether they are beamed sequentially or simultaneously, is termed the isocenter, and to maximize biological effectiveness the isocenter must be precisely collocated with the target growth.

Irradiation treatment is performed on a target tissue in a well defined process. In a first stage, known as the treatment planning stage, the target tissue is imaged and a treatment plan comprising dosage, patient position, and irradiation angles are defined. Furthermore, placement markers are defined, so as to ensure that subsequent irradiation sessions are properly targeted. Irradiation is then performed, responsive to the developed treatment plan, at a plurality of treatment sessions over a period of time, each session being known as a fraction. At each such fraction, care must be taken to ensure proper patient positioning, responsive to the placement markers, so as to avoid damage to organs in vicinity of the target tissue. Positioning of the patient responsive to the markers is performed based on visualization of the patient, responsive to the defined markers.

During the course of the treatment, through a plurality of fractions, anatomical changes can occur in the patient. In particular, topological and morphological changes can occur in the target tissue and/or organs at risk and their milieu. Therefore, the treatment plan is no longer accurate as it is based on anatomical information which has since changed. If the anatomical changes are significant, the treatment can be ineffective and/or harmful to healthy tissue which is not supposed to be treated.

There is thus a long felt need for an improved treatment arrangement which provides for pre-treatment analysis of anatomical changes and their impact on the projected treatment.

SUMMARY OF THE INVENTION

Accordingly, it is a principal object of the present invention to overcome disadvantages of prior art methods and arrangements of teletherapy. This is provided in the present invention by an apparatus for evaluating a change in radiation distribution within at least a portion of a target tissue of a patient, the apparatus constituted of: a memory having stored thereon parameters of radiation to be output by the irradiation source, the radiation parameters determined responsive to a reference image of the patient target tissue; a processor in communication with the memory; and an output module in communication with the processor, wherein the processor is arranged to: receive a present image of the patient target tissue; determine the expected distribution of radiation within the patient target tissue when output from the irradiation source according to the radiation parameters; determine the difference between the determined distribution and a predetermined distribution parameter; and control the output module to output a signal responsive to the determined difference.

In one embodiment, in the event that the determined difference is greater than a predetermined threshold, the output signal comprises a warning signal indicating that the determined difference is greater than the predetermined threshold. In another embodiment, the output module is in communication with a network, wherein the output signal comprises the determined difference, and wherein the signal is output to the network.

In one embodiment, the received present image comprises an image of a section of the patient comprising the target tissue, wherein the memory further has stored thereon the reference image, wherein the reference image comprises an image of the section of the patient comprising the target tissue, wherein the processor is further arranged to compare contours around a predetermined area of the section of the patient comprising the target tissue in the received present image with contours around the predetermined area of the section of the patient comprising the target tissue in the reference image, and wherein the determination of the expected distribution of radiation is responsive to the comparison of contours. In one further embodiment, the processor is further arranged to determine a vector between the section of the patient comprising the target tissue in the received present image and the section of the patient comprising the target tissue in the reference image, and wherein the determination of the expected distribution of radiation is further responsive to the determined vector.

In one embodiment, the processor is further arranged to: determine a path of radiation in relation to the patient target tissue for the irradiation incidence according to the stored radiation parameters; and control the output module to output the determined path. In another embodiment, the processor is further arranged to: determine the fluence of radiation arranged to flow through a cross section of the patient target tissue for the irradiation incidence according to the stored radiation parameters; and control the output module to output the determined fluence. In another embodiment, the received present image is a computed tomography image.

In one embodiment, the difference determination comprises a determination of the difference between one of: a mean value of expected radiation distribution within the patient target tissue and a mean value radiation parameter; a minimum value of expected radiation distribution within a first predetermined area of the patient target tissue and a minimum radiation parameter; a maximum value of expected radiation distribution within a second predetermined area of the patient target tissue and a maximum radiation parameter; and a volume ratio parameter and a ratio between the volume of an area of the patient target tissue exhibiting an expected radiation distribution greater than a first predetermined value and the volume of an area of the target tissue exhibiting an expected radiation distribution less than a second predetermined value, wherein the first predetermined value is greater than the second predetermined value. In another embodiment, the processor is further arranged to: determine a compensation algorithm responsive to the determined difference; and control the output module to output the determined compensation algorithm, wherein the compensation algorithm comprises one of: a change in the position of the patient in relation to the irradiation source; and a change in the radiation parameters of the irradiation source.

In one independent embodiment, a method of evaluating a change in radiation distribution within a target tissue of a patient is provided, the method comprising: receiving a present image of the patient target tissue; responsive to the received present image, determining the expected distribution of radiation within the patient target tissue for an irradiation incidence according to radiation parameters stored on a memory, the radiation parameters determined responsive to a reference image of the patient target tissue; determining the difference between the determined distribution and a predetermined distribution parameter; and outputting a signal responsive to the determined difference.

In one embodiment, in the event that the determined difference is greater than a predetermined threshold, the output signal comprises a warning signal indicating that the determined difference is greater than the predetermined threshold. In another embodiment, the output signal comprises the determined difference, and wherein the outputting the signal is to a network.

In one embodiment, the received present image comprises an image of a section of the patient comprising the target tissue, wherein the reference image comprises an image of the section of the patient comprising the target tissue, wherein the method further comprises comparing contours around a predetermined area of the section comprising the target tissue in the received present image with contours around the predetermined area of the section of the patient comprising the target tissue in the reference image, and wherein the determining the expected distribution of radiation is responsive to the comparing of contours. In one further embodiment, the method further comprises determining a vector between the section of the patient comprising the target tissue in the received present image and the section of the patient comprising the target tissue in the reference image, wherein the determining the expected distribution of radiation is further responsive to the determined vector.

In one embodiment, the method further comprises: determining a path of radiation in relation to the patient target for the irradiation incidence according to the stored radiation parameters; and outputting the determined path. In another embodiment, the method further comprises: determining the fluence of radiation arranged to flow through a cross section of the patient target tissue for the irradiation incidence according to the stored radiation parameters; and outputting the determined fluence. In another embodiment, the received present image is a computed tomography image.

In one embodiment, the difference determining comprises determining the difference between one of: a mean value of expected radiation distribution within the at least a portion of the patient target tissue and a mean value radiation parameter; a minimum value of expected radiation distribution within a first predetermined area of the patient target tissue and a minimum radiation parameter; a maximum value of expected radiation distribution within a second predetermined area of the patient target tissue and a maximum radiation parameter; and a volume ratio parameter and a ratio between the volume of an area of the patient target tissue exhibiting an expected radiation distribution greater than a first predetermined value and the volume of an area of the patient target tissue exhibiting an expected radiation distribution less than a second predetermined value, wherein the first predetermined value is greater than the second predetermined value. In another embodiment, the method further comprises: determining a compensation algorithm responsive to the determined difference; and outputting the determined compensation algorithm, wherein the compensation algorithm comprises one of: a change in the position of the patient in relation to an irradiation source arranged to provided the irradiation incidence according to the stored radiation parameters; and a change in the radiation parameters of the irradiation source.

In another independent embodiment, a non-transitory computer readable medium is provided, the non-transitory computer readable medium having instructions stored thereon, which, when executed by one or more processors, causes the one or more processors to perform operations, the operations comprising: receiving a present image of a patient target tissue; responsive to the received present image, determining the expected distribution of radiation within the patient target tissue for an irradiation incidence according to radiation parameters stored on a memory, the radiation parameters determined responsive to a reference image of the patient target tissue; determining the difference between the determined distribution and a predetermined distribution parameter; and outputting a signal responsive to the determined difference.

In one embodiment, in the event that the determined difference is greater than a predetermined threshold, the output signal comprises a warning signal indicating that the determined difference is greater than the predetermined threshold. In another embodiment, the output signal comprises the determined difference, wherein the outputting the signal is to a network. In another embodiment, the received present image comprises an image of a section of the patient comprising the target tissue, wherein the reference image comprises an image of the section of the patient comprising the target tissue, wherein the operations further comprise comparing contours around a predetermined area of the section comprising the target tissue in the received present image with contours around the predetermined area of the section of the patient comprising the target tissue in the reference image, and wherein the determining of the expected distribution of radiation is responsive to the comparing of contours.

In one embodiment, the operations further comprise determining a vector between the section of the patient comprising the target tissue in the received present image and the section of the patient comprising the target tissue in the reference image, wherein the determining of the expected distribution of radiation is further responsive to the determined vector. In another embodiment, the operations further comprise: determining a path of radiation in relation to the patient target tissue for an irradiation incidence according to the stored radiation parameters; and outputting the determined path.

In one embodiment, the operations further comprise: determining the fluence of radiation arranged to flow through a cross section of the patient target tissue for an irradiation incidence according to the stored radiation parameters; and outputting the determined fluence. In another embodiment, the received present image is a computed tomography image.

In one embodiment, the difference determining comprises determining the difference between one of: a mean value of expected radiation distribution within the patient target tissue and a mean value radiation parameter; a minimum value of expected radiation distribution within a first predetermined area of the patient target tissue and a minimum radiation parameter; a maximum value of expected radiation distribution within a second predetermined area of the patient target tissue and a maximum radiation parameter; and a volume ratio parameter and a ratio between the volume of an area of the patient target tissue exhibiting an expected radiation distribution greater than a first predetermined value and the volume of an area of the patient target tissue exhibiting an expected radiation distribution less than a second predetermined value, wherein the first predetermined value is greater than the second predetermined value. In another embodiment, the operations further comprise: determining a compensation algorithm responsive to the determined difference; and outputting the determined compensation algorithm, wherein the compensation algorithm comprises one of: a change in the position of the patient in relation to an irradiation source arranged to provided the irradiation incidence according to the stored radiation parameters; and a change in the radiation parameters of the irradiation source.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION OF THE PREFERRED EMBODIMENTS

Figure 1:
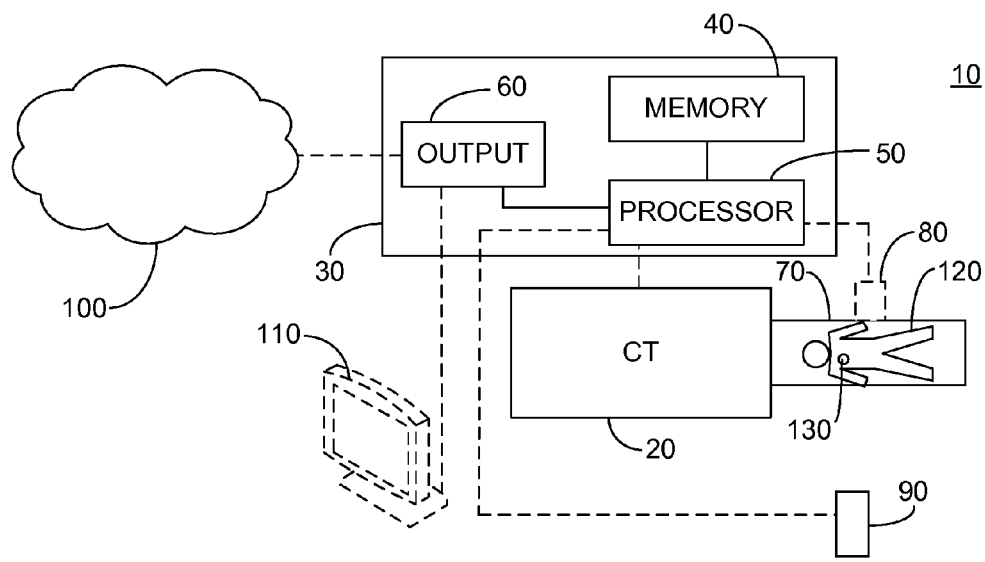
FIG. 1 illustrates a high level schematic diagram of an apparatus for evaluating a change in radiation distribution within at least a portion of a target tissue of a patient.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 2A:
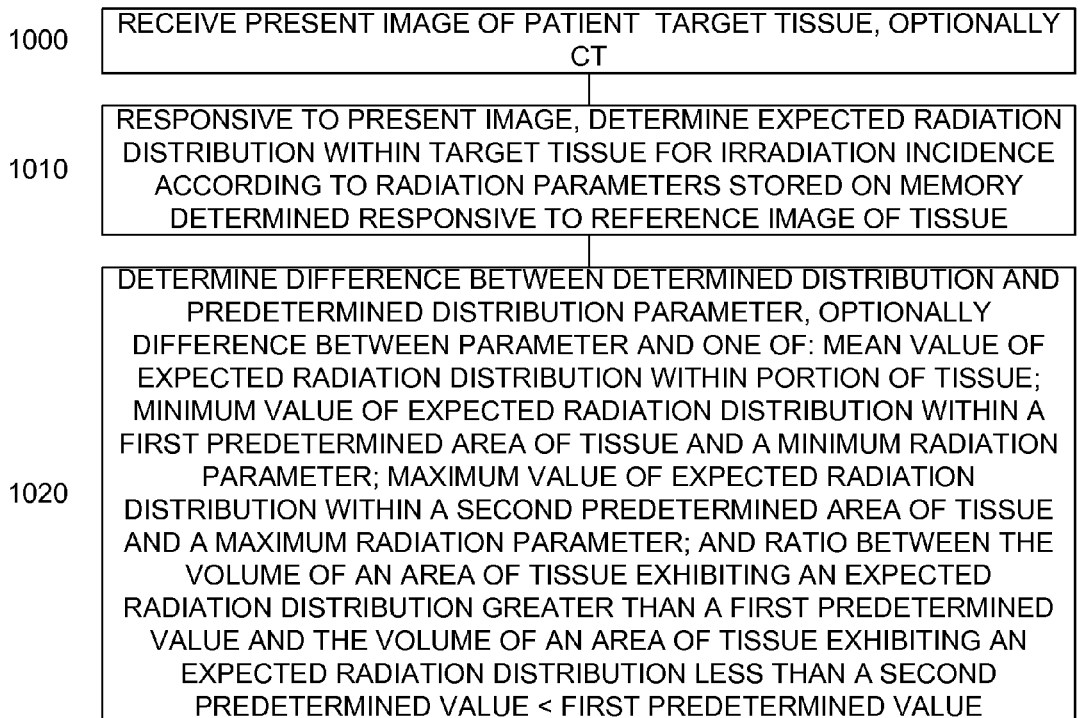
FIGS. 2A-2B illustrate a high level flow chart of a method of operation of the apparatus of FIG. 1.
Figure 2B:
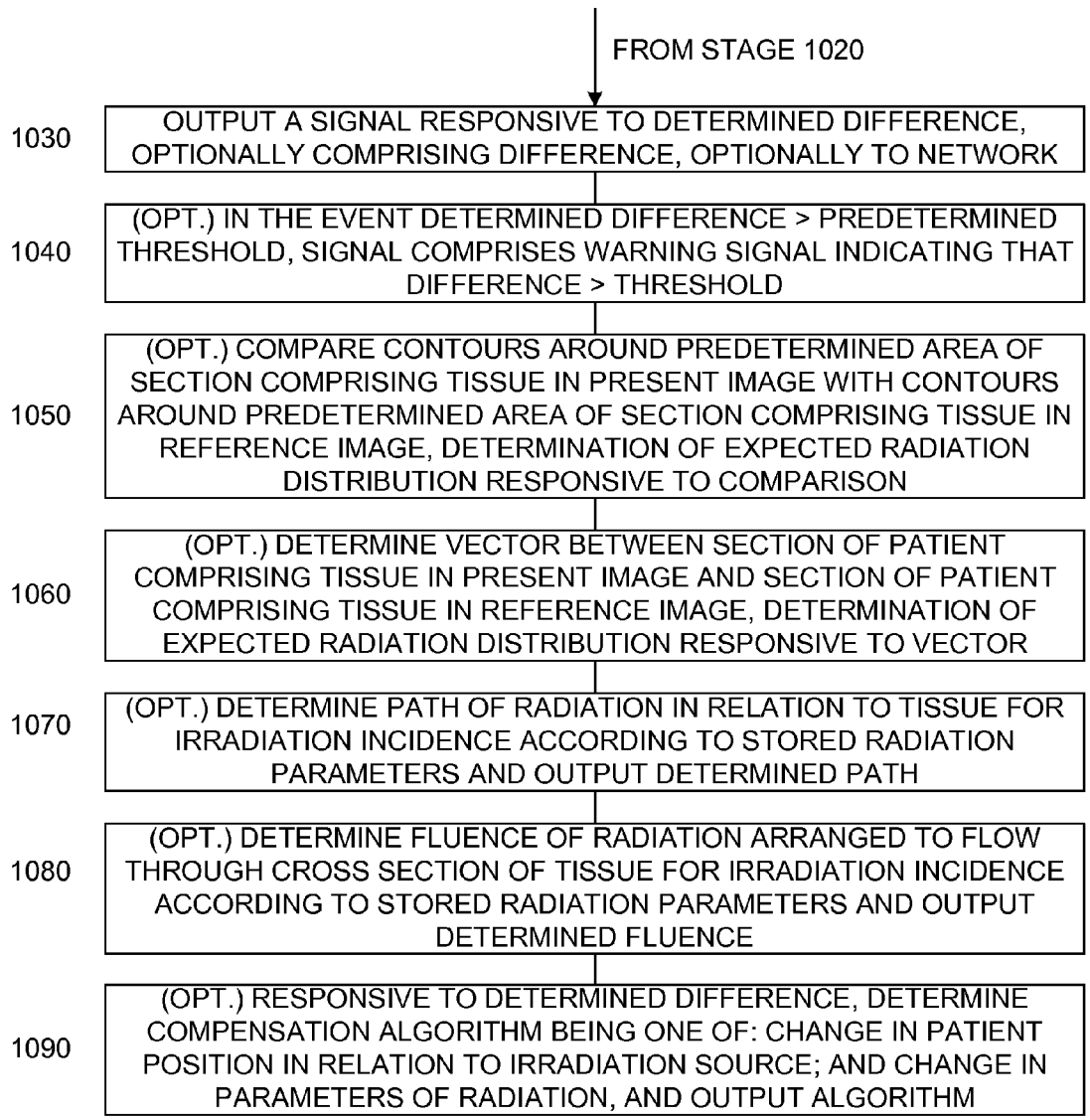

FIG. 1 illustrates a high level schematic diagram of a teletherapy treatment arrangement 10 and FIGS. 2A-2B illustrate a high level flow chart of a method of operation of teletherapy treatment arrangement 10, the FIGs. being described together. Teletherapy treatment arrangement 10 comprises: an imager 20; a control circuitry 30, comprising a memory 40, a processor 50 and an output module 60; a patient platform 70; an optional patient positioner 80; a treatment irradiation source 90; and an optional display 110. A network 100 is further illustrated. A patient 120 exhibiting a target tissue 130 is further illustrated, patient 120 secured to patient platform 70. In one embodiment, imager 20 is a 3 dimensional imager. In another embodiment, imager 20 comprises one or more of: a computed tomography (CT) imager; an ultrasound imager; a magnetic resonance imager; a fluoroscopy imager; a positron emission tomography imager; and a single photon emission computed tomography imager. In one embodiment, control circuitry 30 is implemented as a general purpose computer. In one non-limiting embodiment, processor 50 is arranged to implement computer readable instructions stored on memory 40. In another non-limiting embodiment, the operation of processor 50 is implemented by dedicated hardware of processor 50. In one embodiment, treatment irradiation source 90 is a fixed beam irradiation source, i.e. treatment irradiation source 90 is in a fixed position.

In one embodiment, memory 40 has stored thereon parameters of radiation to be output by treatment irradiation source 90, the radiation parameters determined responsive to a reference image of target tissue 130 taken during the treatment planning phase. In one further embodiment, the radiation parameters are determined for when target tissue 130 is in a predetermined position in relation to treatment irradiation source 90 and the predetermined position is stored on memory 40. In one embodiment, the radiation parameters comprise: the fluence of each beam of radiation to be output by treatment irradiation source 90; and the angle of each beam of radiation, without limitation. In another embodiment, the reference image is additionally stored on memory 40. In one embodiment, the reference image is a CT image. In another embodiment, the reference image comprises an image of the section of patient 120 comprising target tissue 130. In one embodiment, the stored reference image exhibits a plurality of placement markers for identifying predetermined points and/or areas of patient 120. In another embodiment, memory 40 has stored thereon a information regarding a plurality of placement markers for identifying predetermined points and/or areas of patient 120, optionally illustrated over a simulated image of patient 120.

Patient platform 70 is illustrated in a horizontal position, however this is not meant to be limiting in any way and patient platform 70 can be in a vertical position with imager 20 being arranged to image patient 120 while in a vertical position. In one embodiment, network 100 is any of: a cellular network; the internet; and an internal medical center communications network, without limitation. In one embodiment, optional display 110 comprises an audible alarm.

Processor 50 is in communication with memory 40 and output module 60 and is optionally in communication with imager 20, optional patient positioner 80 and treatment irradiation source 90. Output module 60 is in one embodiment in communication with network 100 and in another embodiment is in communication with optional display 110. Optional patient positioner 80 is in communication with patient platform 70 and is arranged to articulate patient platform 70 to a desired position.

In operation, in stage 1000 of FIG. 2A a present image of target tissue 130 is imaged by imager 20 and received by processor 50. In one embodiment, target tissue 130 is a portion of a tissue of patient 120. The term "present image" means an image taken prior to a treatment fraction. In particular, in one embodiment the present image is taken no more than a predetermined temporal period prior to the current treatment fraction, the predetermined temporal period being such that no substantial changes should occur in any organs and/or tissues of patient 120 before the treatment fraction. Preferably, the present image is taken just prior to the treatment fraction, optionally inside the treatment room.

In one embodiment, the present image comprises an image of the section of patient 120 comprising target tissue 130. In one embodiment, imager 20 is controlled by processor 50. In another embodiment, prior to imaging by imager 20, processor 50 controls optional patient positioner 80 to position patient platform 70 such that target tissue 130 is in the predetermined position in relation to treatment irradiation source 90 stored on memory 40. In another embodiment, optional patient positioner 80 is controlled by a control mechanism external of processor 50. In one embodiment, where processor 50 is not in communication with imager 20, processor 50 is arranged to receive the present image from any of: a physical media, such as a compact disc (CD); and a network connection, without limitation.

In stage 1010, responsive to the received present image of stage 1000, processor 50 is arranged to determine an expected distribution of radiation within target tissue 130 for an irradiation incidence from treatment irradiation source 90 according to the predetermined radiation parameters stored on memory 40, which as described above were determined responsive to a reference image of target tissue 130. In one embodiment, target tissue 130 is identified responsive to placement markers stored on memory 40, as described above. In one embodiment, processor 50 is arranged to determine the expected radiation distribution responsive to a proton dose engine. In another embodiment, processor 50 is arranged to create a dose-volume histogram (DVH) of the determined expected radiation distribution within target tissue 130.

In stage 1020, processor 50 is further arranged to determine the difference between the determined radiation distribution of stage 1010 and one or more predetermined distribution parameters. In one embodiment, the predetermined distribution parameters are determined during the treatment planning phase and are stored on memory 40. In another embodiment, the one or more predetermined distribution parameters is the expected radiation distribution within target tissue 130 determined responsive to the reference image of target tissue 130 and in one further embodiment comprises a DVH of the expected radiation distribution. In one embodiment, as will be described below, the one or more predetermined distribution parameters comprises one or more of: a mean radiation parameter; a minimum radiation parameter; maximum radiation parameter; and a volume radiation parameter.

In one embodiment, the difference determination comprises one or more of: a determination of the difference between a mean value of the determined expected radiation distribution within target tissue 130 and a mean radiation parameter; a determination of the difference between a minimum value of expected radiation distribution within a first predetermined area of target tissue 130 and a minimum radiation parameter; a determination of the difference between a maximum value of expected radiation distribution within a second predetermined area of target tissue 130 and a maximum radiation parameter; and a determination of the difference between a volume ratio parameter and a ratio between the volume of an area of target tissue 130 exhibiting an expected radiation distribution greater than a first predetermined value and the volume of an area of target tissue 130 exhibiting an expected radiation distribution less than a second predetermined value, the first predetermined value being greater than the second predetermined value.

In stage 1030 of FIG. 2B, processor 50 is arranged to control output module 60 to output a signal responsive to the determined difference of stage 1030. In one embodiment, the output signal comprises the determined difference. In another embodiment, the output signal further comprises information regarding the determined expected radiation distribution of stage 1010. In another embodiment, the signal is output to network 100 and in one further embodiment the signal is output to a particular network address of network 100, the network address preferably associated with one or more medical personnel. In such an embodiment, the one or more medical personnel can review the received signal, and in one embodiment the determined difference, and decide if any adjustment is necessary for the position of patient 120 and/or the radiation parameters of treatment irradiation source 90. In one embodiment, the signal is output to optional display 110.

In optional stage 1040, in the event the determined difference of stage 1020 is greater than a predetermined threshold, the output signal of stage 1030 comprises a warning signal indicating that the determined difference is greater than the predetermined threshold. In one embodiment, the signal is output to optional display 110 and in one further embodiment the signal is arranged to illustrate a warning on optional display 110. In the embodiment where an audible alarm is provided on optional display 110, the output signal is arranged to control the audible alarm to output a warning sound.

In one embodiment, more than one predetermined threshold is provided. In such an embodiment, processor 50 is arranged to determine which of the predetermined thresholds the determined difference is greater than and further determine which of those predetermined thresholds exhibit the greatest value. In one further embodiment the output signal provides a warning signal responsive to the determined predetermined threshold. For example, in one embodiment three predetermined thresholds are provided:

an adapting threshold; a warning threshold exhibiting a value greater than the adapting threshold; and a stopping threshold exhibiting a value greater than the warning threshold. In the event that the determined difference is greater than the adapting threshold and less than the warning threshold, the output signal indicates that an adaptation of the treatment is necessary and optionally supplies information on the necessary adjustments, as will be described in relation to optional stage 1090. In such a case, the radiology technician, or other medical personnel, can adjust the position of the patient or the radiation parameters of treatment irradiation source 90 in accordance with the received signal, as will be described below.

In the event that the determined difference is greater than the warning threshold and less than the stopping threshold, the output signal indicates that a significant deviation from the predetermined distribution parameters exists and approval from an authorized physician is necessary for continuation of the treatment, optionally with adjustments as described above. In the event that the determined difference is greater than the stopping threshold, the output signal indicates that the deviation from the predetermined distribution parameters is too great and the treatment must be discontinued and a new treatment plan is necessary. In the event that the determined difference is not greater than the adapting threshold, the output signal indicates that the treatment may proceed.

In optional stage 1050, processor 50 is arranged to compare the received present image of stage 1000 with the reference imaged stored on memory 40 and determine anatomical changes that occurred in patient 120 during the period from when the reference image was taken until the present image was taken. As described above, in one embodiment the reference image and the present image each comprise an image of the section of patient 120 comprising target tissue 130. In one embodiment, the comparison comprises comparing contours around at least one predetermined area of the section of patient 120 comprising target tissue 130 in the received present image with contours around the at least one predetermined area of the section of patient 120 comprising target tissue 130 in the reference image. Preferably, the predetermined area is defined as part of the radiation parameters stored on memory 40. In one embodiment, the at least one predetermined area of patient 120 is identified responsive to placement markers stored on memory 40, as described above. The determination of the expected radiation distribution of stage 1010 is responsive to the image comparison, in one particular embodiment responsive to the determined anatomical changes. In one particular embodiment, memory 40 further has stored thereon a previously determined expected radiation distribution determined responsive to the reference image. In such an embodiment, the determination of the expected radiation distribution of stage 1010 is accomplished by adjusting the results of the stored determined expected radiation distribution responsive to the determined anatomical changes of patient 120. Thus, the expected radiation distribution of stage 1010 is determined responsive to an adjustment of a previously determined expected radiation distribution and the expected radiation distribution does need to be calculated in its entirety.

In optional stage 1060, processor 50 is further arranged to determine a transformation vector between the section of patient 120 comprising target tissue 130 in the received present image of stage 1000 and the section of patient 120 comprising target tissue 130 in the reference image. In particular, typically the position of patient 120 when the present image is taken is not exactly the same position as the position which patient 120 was in when the reference image was taken and therefore the position of target tissue 130 in relation to treatment irradiation source 90 differs in the reference image and the present image. In the embodiment where processor 50 is arranged to determine the expected radiation distribution responsive to a comparison of the present image with the reference image, as described above in relation to optional stage 1050, processor 50 utilizes the determined transformation vector to remove from the calculations the changes caused by the positioning difference of patient 120.

In optional stage 1070, processor 50 is further arranged to determine a path of the radiation in relation to target tissue 130 for an irradiation incidence from treatment irradiation source 90 according to the radiation parameters stored on memory 40. Processor 50 is further arranged to control output module 60 to output the determined radiation path. In one embodiment, the determined radiation path is output to network 100 and in another embodiment the determined radiation path is displayed by optional display 110. In optional stage 1080, processor 50 is further arranged to determine the fluence of radiation arranged to flow through a particular cross section of target tissue 130 for an irradiation incidence from treatment irradiation source 90 according to the radiation parameters stored on memory 40. Processor 50 is further arranged to control output module 60 to output the determined radiation fluence. In one embodiment, the determined radiation fluence is output to network 100 and in another embodiment the determined radiation fluence is displayed by optional display 110.

In optional stage 1090, processor 50 is further arranged to determine a compensation algorithm responsive to the determined difference of stage 1020. The compensation algorithm is determined so as to adjust the expected radiation distribution to reduce the difference between the expected radiation distribution and the predetermined distribution parameters. In one embodiment, the compensation algorithm comprises one of: a change in the position of patient 120 in relation to treatment irradiation source 90, thereby adjusting the impact angle of radiation with target tissue 130 when output from treatment irradiation source 90; and a change in the parameters of radiation output by treatment irradiation source 90, such as the angle and/or fluence of one or more radiation beams. Processor 50 is further arranged to control output module 60 to output the determined compensation algorithm. In one embodiment, the determined compensation algorithm is output to network 100 and in another embodiment the determined compensation algorithm is displayed by optional display 110.

In one embodiment, stages 1000-1090 are performed online, the term online being defined for the purpose of this document as meaning during a time period short enough such that a treatment operator receives the output signal of stage 1030, or any of optional stages 1040-1090, and can act thereon prior to irradiation of patient 120. Preferably, as described above, the irradiation can be prevented in the event that irradiation is contraindicated by the output signal of stage 1030 or optional stage 1040. As described above, in one embodiment stages 1000-1090 are performed when patient 120 is inside the treatment room.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

The terms "include", "comprise" and "have" and their conjugates as used herein mean "including but not necessarily limited to".

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

We claim:

1. An apparatus for evaluating a change in expected radiation distribution within a target tissue of a patient, the apparatus comprising:
    a memory having stored thereon parameters of radiation to be output by an irradiation source, the radiation parameters determined responsive to a reference image of the patient target tissue;
    a processor in communication with said memory; and
    an output in communication with said processor, wherein said processor is arranged to:
        receive a present image of the patient target tissue;
        responsive to said received present image, determine an the expected distribution of radiation within the patient target tissue for an irradiation incidence according to the stored radiation parameters;
        determine a difference between said determined distribution and a predetermined distribution parameter; and
        prior to the output of radiation by the irradiation source, control said output to output a signal responsive to said determined difference,
    wherein said determined difference comprises a determination of a difference of a volume ratio parameter and a ratio between a volume of an area of the patient target tissue wherein said determined radiation distribution is greater than a first predetermined value and the volume of an area of the target tissue wherein said determined radiation distribution is less than a second predetermined value, wherein said first predetermined value is greater than said second predetermined value.

2. The apparatus of claim 1, wherein responsive to said determined difference being greater than a predetermined threshold, said output signal comprises a warning signal indicating that said determined difference is greater than the predetermined threshold.

3. The apparatus of claim 1, wherein said output is in communication with a network,
    wherein said output signal comprises said determined difference, and
    wherein said signal is output to the network.

4. The apparatus of claim 1, wherein said received present image comprises an image of a section of the patient comprising the target tissue,
    wherein said memory further has stored thereon the reference image, wherein the reference image comprises an image of the section of the patient comprising the target tissue,
    wherein said processor is further arranged to compare contours around a predetermined area of the section of the patient comprising the target tissue in said received present image with contours around the predetermined area of the section of the patient comprising the target tissue in the reference image, and
    wherein said determination of the expected distribution of radiation is responsive to said comparison of contours.

5. The apparatus of claim 4, wherein said processor is further arranged to determine a vector between the section of the patient comprising the target tissue in said received present image and the section of the patient comprising the target tissue in the reference image, and
    wherein said determination of the expected distribution of radiation is further responsive to said determined vector.

6. The apparatus of claim 1, wherein said processor is further arranged to:
    determine a path of radiation in relation to the patient target tissue for the irradiation incidence according to the stored radiation parameters; and
    control said output to output said determined path.

7. The apparatus of claim 1, wherein said processor is further arranged to:
    determine a fluence of radiation arranged to flow through a cross section of the patient target tissue for an irradiation incidence according to the stored radiation parameters; and
    control said output to output said determined fluence.

8. The apparatus of claim 1, wherein said received present image is a computed tomography image.

9. The apparatus of claim 1, wherein said processor is further arranged to:
    determine a compensation algorithm responsive to said determined difference; and
    control said output to output said determined compensation algorithm,
    wherein said compensation algorithm comprises one of: a change in the position of the patient in relation to the irradiation source; and a change in the radiation parameters of the irradiation source.

10. A method of evaluating a change in radiation distribution within a target tissue of a patient, the method comprising:
    providing a processor;
    receiving by said provided processor a present image of the patient target tissue;
    responsive to said received present image, said provided processor determining an expected distribution of radiation within the patient target tissue for an irradiation incidence according to radiation parameters stored on a memory, the radiation parameters determined responsive to a reference image of the patient target tissue;
    said provided processor determining a difference between said determined distribution and a predetermined distribution parameter; and
    said processor outputting a signal responsive to said determined difference prior to an output of radiation by an irradiation source, wherein said difference determining comprises determining a difference between a volume ratio parameter and a ratio between a volume of an area of the patient target tissue exhibiting an expected radiation distribution greater than a first predetermined value and the volume of an area of the patient target tissue exhibiting an expected radiation distribution less than a second predetermined value, wherein said first predetermined value is greater than said second predetermined value.

11. The method of claim 10, wherein responsive to said determined difference being greater than a predetermined threshold, said output signal comprises a warning signal indicating that said determined difference is greater than the predetermined threshold.

12. The method of claim 10, wherein said output signal comprises said determined difference, and
wherein said outputting said signal is to a network.

13. The method of claim 10, wherein said received present image comprises an image of a section of the patient comprising the target tissue,
wherein the reference image comprises an image of the section of the patient comprising the target tissue,
wherein the method further comprises said provided processor comparing contours around a predetermined area of the section comprising the target tissue in said received present image with contours around the predetermined area of the section of the patient comprising the target tissue in the reference image, and
wherein said determining the expected distribution of radiation is responsive to said comparing of contours.

14. The method of claim 13, further comprising said provided processor determining a vector between the section of the patient comprising the target tissue in said received present image and the section of the patient comprising the target tissue in the reference image,
wherein said determining the expected distribution of radiation is further responsive to said determined vector.

15. The method of claim 10, further comprising:
said provided processor determining a path of radiation in relation to the patient target tissue for the irradiation incidence according to the stored radiation parameters; and said provided processor outputting said determined path.

16. The method of claim 10, further comprising:
said provided processor determining a fluence of radiation arranged to flow through a cross section of the patient target tissue for an irradiation incidence according to the stored radiation parameters; and
said provided processor outputting said determined fluence.

17. The method of claim 10, wherein said received present image is a computed tomography image.

18. The method of claim 10, further comprising:
said provided processor determining a compensation algorithm responsive to said determined difference; and
said provided processor outputting said determined compensation algorithm, wherein said compensation algorithm comprises one of: a change in the position of the patient in relation to the irradiation source arranged to provide the irradiation incidence according to the stored radiation parameters; and a change in radiation parameters of the irradiation source.

* * * * *